(12) United States Patent
Maggioni

(10) Patent No.: US 7,632,986 B1
(45) Date of Patent: Dec. 15, 2009

(54) LETTUCE VARIETY ISI 45125 AND METHOD OF PRODUCTION

(75) Inventor: Alessandro Maggioni, Fidenza (IT)

(73) Assignee: ISI Sementi-SpA, Fidenza (IT)

( * ) Notice: Subject to any disclaimer, the term of this patent is extended or adjusted under 35 U.S.C. 154(b) by 238 days.

(21) Appl. No.: 11/644,452

(22) Filed: Dec. 21, 2006

Related U.S. Application Data

(60) Provisional application No. 60/752,778, filed on Dec. 21, 2005.

(51) Int. Cl.
*A01H 1/00* (2006.01)
*A01H 5/00* (2006.01)
*A01H 5/10* (2006.01)

(52) U.S. Cl. .............. 800/305; 435/410; 800/260; 800/298

(58) Field of Classification Search .............. None
See application file for complete search history.

(56) References Cited

U.S. PATENT DOCUMENTS 7,126,045 B2   10/2006   Knerr

*Primary Examiner*—David H Kruse

(74) *Attorney, Agent, or Firm*—Morrison & Foerster LLP

(57) ABSTRACT

Lettuce variety ISI 45125 is described.

15 Claims, No Drawings

LETTUCE VARIETY ISI 45125 AND METHOD OF PRODUCTION

I. RELATED APPLICATION

This application claims the benefit under 35 USC 119(e) of U.S. Provisional Application No. 60/752,778, filed Dec. 21, 2005, the content of which is hereby incorporated by reference in its entirety.

II. FIELD OF THE INVENTION

The present invention is directed to new varieties of lettuce, *Lactuca sativa*.

III. BACKGROUND OF THE INVENTION

Lettuce is an important crop consumed worldwide. Even though lettuce is a popular crop, there is a need to develop new varieties which display improved characteristics.

IV. SUMMARY OF THE INVENTION

In order to meet these needs, the present invention is directed to improved lettuce varieties. In one embodiment, the present invention is directed to lettuce, *Lactuca sativa*, seed designated as ISI 45125 having ATCC Accession Number PTA-8182. In one embodiment, the present invention is further directed to a lettuce, *Lactuca sativa* plant and parts isolated therefrom produced by growing ISI 45125 lettuce seed. In another embodiment, the present invention is further directed to a *Lactuca sativa* plant and parts isolated therefrom having all the physiological and morphological characteristics of a *Lactuca sativa* plant produced by growing ISI 45125 lettuce seed having ATCC Accession Number PTA-8182. In another embodiment, the present invention is further directed to an $F_1$ hybrid lettuce, *Lactuca sativa* seed, plants grown from the seed and a head isolated therefrom having ISI 45125 as a parent wherein ISI 45125 is grown from ISI 45125 lettuce seed having ATCC Accession Number PTA-8182.

Lettuce plant parts include lettuce heads, lettuce leaves, parts of lettuce leaves, pollen, ovules, flowers and the like. In another embodiment, the present invention is further directed to lettuce heads, lettuce leaves, parts of lettuce leaves, flowers, pollen and ovules isolated from ISI 45125 lettuce plants. In another embodiment, the present invention is further directed to tissue culture of ISI 45125 lettuce plants.

In another embodiment, the present invention is further directed to packaging material containing ISI 45125 plant parts. Such packaging material includes but is not limited to boxes, plastic bags, etc. The ISI 45125 plant parts may be combined with lettuce plant parts of other plant varieties.

In another embodiment, the present invention is further directed to a method of selecting lettuce plants comprising a) growing ISI 45125 lettuce plants wherein the ISI 45125 plants are grown from lettuce seed having ATCC Accession Number PTA-8182 and b) selecting a plant from step a). In another embodiment, the present invention is further directed to lettuce plants, plant parts and seeds produced by the lettuce plants wherein the lettuce plants are isolated by the selection method of the invention.

In another embodiment, the present invention is further directed to a method of breeding lettuce plants comprising crossing a lettuce plant with a plant grown from ISI 45125 lettuce seed having ATCC Accession Number PTA-8182. In another embodiment, the present invention is further directed to lettuce plants, lettuce parts from the lettuce plants and seeds produced therefrom where the lettuce plant is isolated by the breeding method of the invention.

V. DETAILED DESCRIPTION OF THE INVENTION

Origin and Breeding History of the Varieties

ISI 45271

45271 is a red lollo lettuce variety developed from a hand pollinated cross of the varieties ISI 45001 and ISI 45003, both available from ISI Sementi in Italy. The initial cross was made in Fidenza (PR), Italy. The F1 seed harvested was designated as 33-0501001. The cross was made to produce a variety with good bolting resistance for summer cultivation.

The following year, approximately 50 plants of the F1 seed were planted in Cesena (FC), Italy for seed increase. The block was rogued eliminating the self pollination plants. The F2 seed was harvested individually.

More than 30 F2 populations were planted in a research and development field trial in Cesena (FC), Italy the following year. Individual F2 plants were selected at market maturity for particular distinguishing characteristics in type, size, color, and days to bolting.

The F3 seed were trialed throughout the growing season in years 3 and 4 in Fidenza (PR), Italy.

A selected line was increased in year 5. Early bolting and less dark plants were removed. The plants were harvested individually and the F5 population showed good stability and uniformity.

The F6 seed was uniform and without variants and showed good bolting resistance. ISI 45271 was evaluated and determined to be uniform and stable in commercial trials and seed production for two years.

Objective Description of the Variety ISI 45271

Plant Type
ISI 45271 is plant type Cutting/Leaf.

Seed
The seeds are black in color. The seeds do not require light. The seeds are susceptible to heat dormancy.

Cotyledon to Fourth Leaf Stage
The cotyledons are broad in shape. The shape of the fourth leaf is oval. The length/width index of the fourth leaf is 1/3×10. The apical margin is finely dentate. The basal margin is pinnately lobed. The undulation is medium. The green color is medium green. The distribution of the anthocyanin is throughout and the concentration is intense. Rolling is absent. It is uncupped. Reflexing is present in the lateral margins.

Mature Leaves

Margin
The incision depth is moderate. The indentation is deeply dentate. The undulations of the apical margin are strong. The green color is medium green.

The anthocyanin distribution is throughout and the concentration is intense. It is large in size. It is glossy. There is strong blistering. The leaf is thin. The trichomes are absent.

Plant
The spread of frame leaves is 35 cm. The head diameter is 20 cm. The head shape is non-heading. The head weight is 300 g. The head firmness is loose. The butt is rounded. The midrib is moderately raised. The diameter at base of head is 17 mm. The ratio of head diameter/core diameter is 13.3. The core height from base of head to apex is 35 mm.

Bolting

The number of days from first water date to seed stalk emergence was 50. The bolting class is slow. The height of mature seed stalk is 65. The spread of bolter plant is 28 cm. The bolter leaves are curved. The margin is dentate. The color is medium green. The bolter habit of the terminal inflorescence is present. The bolter habit of the lateral shoots is present. The bolter habit of the basal side shoots is present.

Maturity

The season picked was summer. The earliness of harvest-mature head formation was 35 days.

Adaptation

The primary regions of adaptation are Southwest, North Central, West Coast, Southeast, and Northeast. The ISI 45271 adapted in the Southwest in the spring, summer, and fall seasons. It did not adapt in the winter. The soil type was both organic and mineral.

Viral Diseases

The ISI 45271 is moderately susceptible/moderately resistant to big vein. It is resistant to lettuce mosaic. It is susceptible to cucumber mosaic, tomato bushy stunt, turnip mosaic, beet western yellows and lettuce infectious yellows.

Fungal/Bacterial Diseases

The ISI 45271 is susceptible to corky root rot, botrylis, verticillium wilt, bacterial leaf spot, and anthracnose. It is moderately susceptible/moderately resistant to powdery mildew, sclerotinla drop, and bacterial soft rot. It is resistant to the CAI-CAVI races of downy mildew.

Insects

The ISI 45271 is susceptible to cabbage loopers, root aphids, green peach aphid, and lettuce aphid, and pea leafminer.

Physiological Stresses

The ISI 45271 is susceptible to cold and brown rib. It is moderately susceptible/moderately resistant to tipburn, drought, and salt. It is resistant to heat.

Post Harvest Stress

The ISI 45271 is susceptible to pink rib, russet spotting, rusty brown discoloration, internal rib necrosis, and brown stain.

Comparisons to ISI 45271

Lollo Rossa

The most similar variety used as a comparison to the ISI 45271 is Lollo Rossa.

Plant Type

Lollo Rossa is plant type Cutting/Leaf.

Seed

The seeds are black in color. The seeds do not require light. The seeds are susceptible to heat dormancy.

Cotyledon to Fourth Leaf Stage

The cotyledons are broad in shape. The shape of the fourth leaf is oval. The length/width index of the fourth leaf is 1/5×10. The apical margin is finely dentate. The basal margin is pinnately lobed. The undulation is medium. The green color is medium green. The distribution of the anthocyanin is throughout. The concentration is intense. Rolling is absent. It is uncupped. Reflexing is present in the lateral margins.

Mature Leaves

Margin

The incision depth is moderate. The indentation is deeply dentate. The undulations of the apical margin are strong. The green color is medium green.

The anthocyanin distribution is throughout and the concentration is intense. It is medium in size. It is glossy. There is strong blistering. The leaf is thin. The trichomes are present.

Plant

The spread of frame leaves is 30 cm. The head diameter is 15 cm. The head shape is non-heading. The head weight is 250 g. The head firmness is loose. The butt is slightly concave. The midrib is moderately raised. The diameter at base of head is 15 mm. The ratio of head diameter/core diameter is 10.0. The core height from base of head to apex is 30 mm.

Bolting

The number of days from first water date to seed stalk emergence was 40. The bolting class is medium. The height of mature seed stalk is 60. The spread of bolter plant is 20 cm. The bolter leaves are curved. The margin is dentate. The color is medium green. The bolter habit of the terminal inflorescence is absent. The bolter habit of the lateral shoots is present. The bolter habit of the basal side shoots is present.

Maturity

The season picked was summer. The earliness of harvest-mature head formation was 30 days.

Viral Diseases

The Lollo Rossa is susceptible to big vein, lettuce mosaic, cucumber mosaic, tomato bushy stunt, turnip mosaic, beet western yellows and lettuce infectious yellows.

Fungal/Bacterial Diseases

The Lollo Rossa is susceptible to corky root rot, botrylis, verticillium wilt, bacterial leaf spot, and anthracnose, powdery mildew, sclerotinla drop, bacterial soft rot, and CAI-CAVI races of downy mildew.

Insects

The Lollo Rossa is susceptible to cabbage loopers, root aphids, green peach aphid, and lettuce aphid, and pea leafminer.

Physiological Stresses

The Lollo Rossa is susceptible to cold, brown rib, tipburn, drought, salt, and heat.

Post Harvest Stress

The Lollo Rossa is susceptible to pink rib, russet spotting, rusty brown discoloration, internal rib necrosis, and brown stain.

Solargo

The standard regional check variety used is Solargo.

Plant Type

Solargo is plant type Cutting/Leaf.

Seed

The seeds are white in color. The seeds do not require light. The seeds are susceptible to heat dormancy.

Cotyledon to Fourth Leaf Stage

The cotyledons are broad in shape. The shape of the fourth leaf is oval. The length/width index of the fourth leaf is 1/4×10. The apical margin is finely dentate. The basal margin is pinnately lobed. The undulation is medium. The green color is medium green. The distribution of the anthocyanin is throughout. The concentration is intense. Rolling is absent. It is uncupped. Reflexing is present in the lateral margins.

Mature Leaves

Margin

The incision depth is moderate. The indentation is deeply dentate. The undulations of the apical margin were strong. The green color is medium green.

The anthocyanin distribution is throughout and the concentration is moderate. It is medium in size. It is glossy. There is strong blistering. The leaf is thin. The trichomes are present.

Plant

The spread of frame leaves is 30 cm. The head diameter is 15 cm. The head shape is non-heading. The head weight is 250 g. The head firmness is loose. The butt is slightly concave. The midrib is moderately raised. The diameter at base of head is 15 mm. The ratio of head diameter/core diameter is 10.0. The core height from base of head to apex is 30 mm.

Bolting

The number of days from first water date to seed stalk emergence was 40. The bolting class is medium. The height of mature seed stalk is 60. The spread of bolter plant is 20 cm. The bolter leaves are curved. The margin is dentate. The color is medium green. The bolter habit of the terminal inflorescence is absent. The bolter habit of the lateral shoots is absent. The bolter habit of the basal side shoots is present.

Maturity

The season picked was summer. The earliness of harvest-mature head formation was 28 days.

Viral Diseases

The Solargo is susceptible to big vein, lettuce mosaic, cucumber mosaic, tomato bushy stunt, turnip mosaic, beet western yellows and lettuce infectious yellows.

Fungal/Bacterial Diseases

The Solargo is susceptible to corky root rot botrylis, verticillium wilt, bacterial leaf spot anthracnose, powdery mildew. It is moderately resistant/moderately susceptible to CAI-CAVI races of downy mildew, sclerotinla drop, and bacterial soft rot.

Insects

The Solargo is susceptible to cabbage loopers, root aphids, green peach aphid, lettuce aphid, and pea leafminer.

Physiological Stresses

The Solargo is susceptible to cold, brown rib, drought, salt, and heat. It is moderately susceptible/moderately resistant to tipburn.

Post Harvest Stress

The Solargo is susceptible to pink rib, russet spotting, rusty brown discoloration, internal rib necrosis, and brown stain.

ISI 45125

45125 is a red lollo lettuce variety developed from a hand pollinated cross of the varieties ISI 45037 and ISI 45312, both available from ISI Sementi in Italy. The initial cross was made in Fidenza (PR), Italy. The F1 seed harvested was designated as 33-0501892. The cross was made to produce a variety with good bolting resistance and red uniform cherry color.

The following year, approximately 40 plants of the F1 seed were planted in Cesena (FC), Italy for seed increase. The block was rogued eliminating the self pollination plants. The F2 seed was harvested individually.

More than 20 F2 populations were planted in a research and development field trial in Cesena (FC), Italy the following year. Individual F2 plants were selected at market maturity for particular distinguishing characteristics in type, size, cherry color, and days to bolting.

The F3 seed were trialed throughout the growing season in years 3 and 4 in Fidenza (PR), Italy.

A selected line was increased in year 5. Early bolting and darker plants were removed. The plants were harvested individually and the F5 population showed good stability and uniformity.

The F6 seed was uniform and without variants and showed good bolting resistance. ISI 45125 was evaluated and determined to be uniform and stable in commercial trials and seed production for two years.

Objective Description of the Variety ISI 45125

Plant Type

ISI 45125 is plant type Cutting/leaf.

Seed

The seeds are white in color. The seeds do not require light. The seeds are susceptible to heat dormancy.

Cotyledon to Fourth Leaf Stage

The cotyledons are broad in shape. The shape of the fourth leaf is oval. The length/width index of the fourth leaf is 1/2×10. The apical margin is finely dentate. The basal margin is pinnately lobed. The undulation is medium. The green color is light green. The distribution of the anthocyanin is throughout and the concentration is moderate. Rolling is absent. It is uncupped. Reflexing is present in the lateral margins.

Mature Leaves

Margin

The incision depth is moderate. The indentation is deeply dentate. The undulations of the apical margin are strong. The green color is light green.

The anthocyanin distribution is throughout and the concentration is moderate. It is medium in size. It is glossy. There is strong blistering. The leaf is thin. The trichomes are absent.

Plant

The spread of frame leaves is 30 cm. The head diameter is 17 cm. The head shape is non-heading. The head weight is 240 g. The head firmness is loose. The butt is slightly concave. The midrib is moderately raised. The diameter at base of head is 14 mm. The ratio of head diameter/core diameter is 12.1. The core height from base of head to apex is 35 mm.

Bolting

The number of days from first water date to seed stalk emergence was 51. The bolting class is slow. The height of mature seed stalk is 60. The spread of bolter plant is 20 cm. The bolter leaves are curved. The margin is dentate. The color is medium green. The bolter habit of the terminal inflorescence is present. The bolter habit of the lateral shoots is present. The bolter habit of the basal side shoots is absent.

Maturity

The season picked was summer. The earliness of harvest-mature head formation was 37 days.

Adaptation

The primary regions of adaptation are Southwest, North Central, West Coast, Southeast, and Northeast. The ISI 45125 adapted in the Southwest in the spring and summer seasons. It did not adapt in the fall and winter. The soil type was both organic and mineral.

Viral Diseases

The ISI 45125 is susceptible to big vein, lettuce mosaic, cucumber mosaic, tomato bushy stunt, turnip mosaic, beet western yellows and lettuce infectious yellows.

Fungal/Bacterial Diseases

The ISI 45125 is susceptible to corky root rot, botrylis, verticillium wilt, bacterial leaf spot, powdery mildew, and anthracnose. It is moderately susceptible/moderately resistant to sclerotinla drop and bacterial soft rot. It is resistant to the CAI-CAVI races of downy mildew.

Insects

The ISI 45125 is susceptible to cabbage loopers, root aphids, green peach aphid, and lettuce aphid, and pea leafminer.

Physiological Stresses

The ISI 45125 is susceptible to cold and brown rib. It is moderately susceptible/moderately resistant to tipburn, heat, drought, and salt.

Post Harvest Stress

The ISI 45125 is susceptible to russet spotting, rusty brown discoloration, internal rib necrosis, and brown stain. It is moderately susceptible/moderately resistant to pink rib.

Comparisons to ISI 45125

Lollo Rossa

The most similar variety used as a comparison to the ISI 45271 is Lollo Rossa. Please see description above.

Revolution

The standard regional check variety used is Revolution.

Plant Type

Revolution is plant type Cutting/Leaf

Seed

The seeds are black in color. The seeds do not require light. The seeds are susceptible to heat dormancy.

Cotyledon to Fourth Leaf Stage

The cotyledons are broad in shape. The shape of the fourth leaf is oval. The length/width index of the fourth leaf is 1/5×10. The apical margin is finely dentate. The basal margin is pinnately lobed. The undulation is medium. The green color is medium green. The distribution of the anthocyanin is throughout. The concentration is intense. Rolling is absent. It is uncupped. Reflexing is present in the lateral margins.

Mature Leaves

Margin

The incision depth is moderate. The indentation is deeply dentate. The undulations of the apical margin are strong. The green color is medium green.

The anthocyanin distribution is throughout. The concentration is intense. It is large in size. It is glossy. There is strong blistering. The leaf is thin. The trichomes are absent.

Plant

The spread of frame leaves is 33 cm. The head diameter is 15 cm. The head shape is non-heading. The head weight is 280 g. The head firmness is loose. The butt is slightly concave. The midrib is moderately raised. The diameter at base of head is 15 mm. The ratio of head diameter/core diameter is 10.0. The core height from base of head to apex is 30 mm.

Bolting

The number of days from first water date to seed stalk emergence was 40. The bolting class is medium. The height of mature seed stalk is 65. The spread of bolter plant is 20 cm. The bolter leaves are curved. The margin is dentate. The color is medium green. The bolter habit of the terminal inflorescence is present. The bolter habit of the lateral shoots is present. The bolter habit of the basal side shoots is absent.

Maturity

The season picked was summer. The earliness of harvest-mature head formation was 35 days.

Viral Diseases

The Revolution is susceptible to big vein, lettuce mosaic, cucumber mosaic, tomato bushy stunt, turnip mosaic, beet western yellows and lettuce infectious yellows.

Fungal/Bacterial Diseases

The Revolution is susceptible to corky root rot, CAI-CAVI races of downy mildew, botrylis, verticillium wilt, bacterial leaf spot, powdery mildew, and anthracnose. It is moderately susceptible/moderately resistant to sclerotinla drop and bacterial soft rot.

Insects

The Revolution is susceptible to cabbage loopers, root aphids, green peach aphid, and lettuce aphid, and pea leafminer.

Physiological Stresses

The Revolution is susceptible to cold, brown rib, drought, and salt. It is moderately susceptible/moderately resistant to tipburn and heat.

Post Harvest Stress

The Revolution is susceptible to russet spotting, rusty brown discoloration, internal rib necrosis, brown stain, and pink rib.

ISI 45270

45270 is a red lollo lettuce variety developed from a hand pollinated cross of the varieties ISI 45037 and ISI 45001, both available from ISI Sementi in Italy. The initial cross was made in Fidenza (PR), Italy. The F1 seed harvested was designated as 33-0501097. The cross was made to produce a variety with good bolting resistance and red uniform cherry color and upright standing.

The following year, approximately 50 plants of the F1 seed were planted in Cesena (FC), Italy for seed increase. The block was rogued eliminating the self pollination plants. The F2 seed was harvested individually.

More than 30 F2 populations were planted in a research and development field trial in Cesena (FC), Italy the following year. Individual F2 plants were selected at market maturity for particular distinguishing characteristics in type, size, cherry color, days to bolting, and upright standing.

The F3 seed were trialed throughout the growing season in years 3 and 4 in Fidenza (PR), Italy.

A selected line was increased in year 5. Early bolting, dark and flat plants were removed. The plants were harvested individually and the F5 population showed good stability and uniformity.

The F6 seed was uniform and without variants and showed good bolting resistance. ISI 45270 was evaluated and determined to be uniform and stable in commercial trials and seed production for two years.

Objective Description of the Variety ISI 45270

Plant Type

ISI 45270 is plant type Cutting/Leaf.

Seed

The seeds are black in color. The seeds do not require light. The seeds are susceptible to heat dormancy.

Cotyledon to Fourth Leaf Stage

The cotyledons are broad in shape. The shape of the fourth leaf is oval. The length/width index of the fourth leaf is 1/1×10. The apical margin is finely dentate. The basal margin is pinnately lobed. The undulation is medium. The green color is light green. The distribution of the anthocyanin is throughout. The concentration is moderate. Rolling is absent. It is uncupped. Reflexing is present in the lateral margins.

Mature Leaves

Margin

The incision depth is moderate. The indentation is deeply dentate. The undulations of the apical margin are strong. The green color is light green.

The anthocyanin distribution is throughout and the concentration is moderate. It is medium in size. It is glossy. There is strong blistering. The leaf is thin. The trichomes are absent.

Plant

The spread of frame leaves is 27 cm. The head diameter is 18 cm. The head shape is non-heading. The head weight is 210 g. The head firmness is loose. The butt is slightly concave. The midrib is moderately raised. The diameter at base of head is 16 mm. The ratio of head diameter/core diameter is 12.8. The core height from base of head to apex is 35 mm.

Bolting

The number of days from first water date to seed stalk emergence was 36. The bolting class is rapid. The height of mature seed stalk is 60. The spread of bolter plant is 21 cm. The bolter leaves are curved. The margin is dentate. The color is light green. The bolter habit of the terminal inflorescence is absent. The bolter habit of the lateral shoots is present. The bolter habit of the basal side shoots is absent.

Maturity

The season picked was summer. The earliness of harvest-mature head formation was 28 days.

Adaptation

The primary regions of adaptation are Southwest, North Central, West Coast, Southeast, and Northeast. The ISI 45270 adapted in the Southwest in the spring and summer seasons. It did not adapt in the fall and winter. The soil type was both organic and mineral.

Viral Diseases

The ISI 45270 is susceptible to big vein, lettuce mosaic, cucumber mosaic, tomato bushy stunt, turnip mosaic, beet western yellows and lettuce infectious yellows.

Fungal/Bacterial Diseases

The ISI 45270 is susceptible to corky root rot, botrylis, verticillium wilt, bacterial leaf spot powdery mildew, and anthracnose. It is moderately susceptible/moderately resistant to sclerotinla drop and bacterial soft rot. It is resistant to the CAI-CAVI races of downy mildew.

Insects

The ISI 45270 is susceptible to cabbage loopers, root aphids, green peach aphid, and lettuce aphid, and pea leafminer.

Physiological Stresses

The ISI 45270 is susceptible to cold and brown rib. It is moderately susceptible/moderately resistant to tipburn, heat, drought, and salt.

Post Harvest Stress

The ISI 45270 is susceptible to russet spotting, rusty brown discoloration, internal rib necrosis, and brown stain. It is moderately susceptible/moderately resistant to pink rib.

Comparisons to ISI 45270

Lollo Rossa

The most similar variety used as a comparison to the ISI 45271 is Lollo Rossa. Please see description above.

Solargo

The standard regional check variety used is Solargo. Please see description above.

ISI 47555

47555 is a red oak leaf lettuce variety developed from a hand pollinated cross of the varieties ISI 47005 and Red Salad bowl, both available from ISI Sementi in Italy. The initial cross was made in Fidenza (PR), Italy. The F1 seed harvested was designated as 33-0501121. The cross was made to produce a variety with dark red color and upright standing.

The following year, approximately 20 plants of the F1 seed were planted in Cesena (FC), Italy for seed increase. The block was rogued eliminating the self pollination plants. The F2 seed was harvested individually.

More than 10 F2 populations were planted in a research and development field trial in Cesena (FC), Italy the following year. Individual F2 plants were selected at market maturity for particular distinguishing characteristics in type, size, dark red color, days to bolting, upright standing.

The F3 seed were trialed throughout the growing season in years 3 and 4 in Fidenza (PR), Italy.

A selected line was increased in year 5. Early bolting, less dark and flat plants were removed. The plants were harvested individually and the F5 population showed good stability and uniformity.

The F6 seed was uniform and without variants and showed good bolting resistance. ISI 47555 was evaluated and determined to be uniform and stable in commercial trials and seed production for two years.

Objective Description of the Variety ISI 47555

Plant Type

ISI 47555 is plant type Cutting/Leaf.

Seed

The seeds are white in color. The seeds do not require light. The seeds are susceptible to heat dormancy.

Cotyledon to Fourth Leaf Stage

The cotyledons are broad in shape. The shape of the fourth leaf is pinnately lobed. The length/width index of the fourth leaf is 1/9×10. The apical margin is lobed. The basal margin is entire. The undulation is medium. The green color is light green. The distribution of the anthocyanin is throughout and the concentration is intense. Rolling is absent. It is uncupped. There is no reflexing.

Mature Leaves

Margin

The incision depth is moderate. The indentation is entire. The undulations of the apical margin are moderate. The green color is very light green.

The anthocyanin distribution is throughout and the concentration is intense. It is medium in size. It is moderately glossy. Blistering is absent/slight. The leaf is thin. The trichomes are absent.

Plant

The spread of frame leaves is 23 cm. The head diameter is 26 cm. The head shape is non-heading. The head weight is 180 g. The head firmness is loose. The butt is slightly concave. The midrib is moderately raised. The diameter at base of head is 13 mm. The ratio of head diameter/core diameter is 18.6. The core height from base of head to apex is 60 mm.

Bolting

The number of days from first water date to seed stalk emergence was 33. The bolting class is rapid. The height of mature seed stalk is 70 cm. The spread of bolter plant is 25 cm. The bolter leaves are straight. The margin is entire. The color is light green. The bolter habit of the terminal inflorescence is present. The bolter habit of the lateral shoots is present. The bolter habit of the basal side shoots is absent.

Maturity

The season picked was summer. The earliness of harvest-mature head formation was 27 days.

Adaptation

The primary regions of adaptation are Southwest, North Central, West Coast, Southeast, and Northeast. The ISI 47555 adapted in the Southwest in the spring, summer, and fall seasons. It did not adapt in the winter. The soil type was both organic and mineral.

Viral Diseases

The ISI 47555 is susceptible to cucumber mosaic, tomato bushy stunt, turnip mosaic, beet western yellows and lettuce infectious yellows. It is moderately susceptible/moderately resistant big vein. It is resistant to lettuce mosaic.

Fungal/Bacterial Diseases

The ISI 47555 is susceptible to corky root rot, botrylis, verticillium wilt, bacterial leaf spot, powdery mildew, anthracnose, and bacterial soft rot. It is moderately susceptible/moderately resistant to sclerotinla drop. It is resistant to the CAI-CAVI races of downy mildew.

Insects

The ISI 47555 is susceptible to cabbage loopers, root aphids, green peach aphid, and lettuce aphid, and pea leafminer.

Physiological Stresses

The ISI 47555 is susceptible to heat and brown rib. It is moderately susceptible/moderately resistant to cold, tipburn, heat, drought, and salt.

Post Harvest Stress

The ISI 47555 is susceptible to russet spotting, rusty brown discoloration, internal rib necrosis, brown stain, and pink rib.

Comparisons to 47555

Red Salad Bowl

The most similar variety used as a comparison to the ISI 47555 is Red Salad Bowl.

Plant Type

Red Salad Bowl is plant type Cutting/Leaf.

Seed

The seeds are black in color. The seeds do not require light. The seeds are susceptible to heat dormancy.

Cotyledon to Fourth Leaf Stage

The cotyledons are broad in shape. The shape of the fourth leaf is pinnately lobed. The length/width index of the fourth leaf is 2×10. The apical margin is lobed. The basal margin is entire. The undulation is medium. The green color is medium green. The distribution of the anthocyanin is throughout. The concentration is moderate. Rolling is absent. It is uncupped. There is no reflexing.

Mature Leaves

Margin

The incision depth is moderate. The indentation is entire. The undulations of the apical margin are moderate. The green color is light green.

The anthocyanin distribution is throughout and the concentration is moderate. It is small in size. It is moderately glossy. Blistering is absent/slight. The leaf is thin. The trichomes are present.

Plant

The spread of frame leaves is 20 cm. The head diameter is 20 cm. The head shape is non-heading. The head weight is 150 g. The head firmness is loose. The butt is slightly concave. The midrib is moderately raised. The diameter at base of head is 12 mm. The ratio of head diameter/core diameter is 16.6. The core height from base of head to apex is 65 mm.

Bolting

The number of days from first water date to seed stalk emergence was 30. The bolting class is medium. The height of mature seed stalk is 65 cm. The spread of bolter plant is 22 cm. The bolter leaves are straight. The margin is entire. The color is medium green. The bolter habit of the terminal inflorescence is absent. The bolter habit of the lateral shoots is present. The bolter habit of the basal side shoots is present.

Maturity

The season picked was summer. The earliness of harvest-mature head formation was 23 days.

Viral Diseases

The Red Salad Bowl is susceptible to cucumber mosaic, tomato bushy stunt, turnip mosaic, beet western yellows, lettuce infectious yellows, big vein, and lettuce mosaic.

Fungal/Bacterial Diseases

The Red Salad Bowl is susceptible to corky root rot, botrylis, verticillium wilt, bacterial leaf spot powdery mildew, anthracnose, bacterial soft rot, sclerotinla drop, and the CAI-CAVI races of downy mildew.

Insects

The Red Salad Bowl is susceptible to cabbage loopers, root aphids, green peach aphid, and lettuce aphid, and pea leafminer.

Physiological Stresses

The Red Salad Bowl is susceptible to heat and brown rib, cold, tipburn, heat, drought, and salt.

Post Harvest Stress

The Red Salad Bowl is susceptible to russet spotting, rusty brown discoloration, internal rib necrosis, brown stain, and pink rib.

Cerize

The standard regional check variety used is Cerize.

Plant Type

Cerize is plant type Cutting/Leaf.

Seed

The seeds are black in color. The seeds do not require light. The seeds are susceptible to heat dormancy.

Cotyledon to Fourth Leaf Stage

The cotyledons are broad in shape. The shape of the fourth leaf is pinnately lobed. The length/width index of the fourth leaf is 2/1×10. The apical margin is lobed. The basal margin is entire. The undulation is medium. The green color is medium green. The distribution of the anthocyanin is throughout. The concentration is intense. Rolling is absent. It is uncupped. There is no reflexing.

Mature Leaves

Margin

The incision depth is moderate. The indentation is entire. The undulations of the apical margin are moderate. The green color is light green.

The anthocyanin distribution is throughout and the concentration is intense. It is medium in size. It is moderately glossy. Blistering is absent/slight. The leaf is thin. The trichomes are absent.

Plant

The spread of frame leaves is 21 cm. The head diameter is 22 cm. The head shape is non-heading. The head weight is 165 g. The head firmness is loose. The butt is slightly concave. The midrib is moderately raised. The diameter at base of head is 12 mm. The ratio of head diameter/core diameter is 18.3. The core height from base of head to apex is 60 mm.

Bolting

The number of days from first water date to seed stalk emergence was 35. The bolting class is medium. The height of mature seed stalk is 65 cm. The spread of bolter plant is 23 cm. The bolter leaves are straight. The margin is entire. The color is medium green. The bolter habit of the terminal inflorescence is present. The bolter habit of the lateral shoots is present. The bolter habit of the basal side shoots is absent.

Maturity

The season picked was summer. The earliness of harvest-mature head formation was 28 days.

Viral Diseases

The Cerize is susceptible to cucumber mosaic, tomato bushy stunt, turnip mosaic, beet western yellows, lettuce infectious yellows, and big vein. It is moderately susceptible/moderately resistant to lettuce mosaic.

Fungal/Bacterial Diseases

The Cerize is susceptible to corky root rot, botrylis, verticillium wilt, bacterial leaf spot, powdery mildew, anthracnose, bacterial soft rot, and sclerotinla drop. It is resistant to the CAI-CAVI races of downy mildew.

Insects

The Cerize is susceptible to cabbage loopers, root aphids, green peach aphid, and lettuce aphid, and pea leafminer.

Physiological Stresses

The Cerize is susceptible to brown rib, cold, heat, and drought. It is moderately susceptible/moderately resistant to tipburn and salt.

Post Harvest Stress

The Cerize is susceptible to russet spotting, rusty brown discoloration, internal rib necrosis, brown stain, and pink rib.

ISI 44038

44038 is a red leaf lettuce variety developed from a hand pollinated cross of the varieties ISI 44009 and ISI 44011, both available from ISI Sementi in Italy. The initial cross was made in Fidenza (PR), Italy. The F1 seed harvested was designated as 33-0501092. The cross was made to produce a variety with dark red color, upright standing and smooth leaves.

The following year, approximately 40 plants of the F1 seed were planted in Cesena (FC), Italy for seed increase. The block was rogued eliminating the self pollination plants. The F2 seed was harvested individually.

More than 25 F2 populations were planted in a research and development field trial in Cesena (FC), Italy the following year. Individual F2 plants were selected at market maturity for particular distinguishing characteristics in type, size, dark red color, days to bolting, upright standing, smooth leaf.

The F3 seed were trialed throughout the growing season in years 3 and 4 in Fidenza (PR), Italy.

A selected line was increased in year 5. Early bolting, less dark and bubbled plants were removed. The plants were harvested individually and the F5 population showed good stability and uniformity.

The F6 seed was uniform and without variants and showed good bolting resistance. ISI 44038 was evaluated and determined to be uniform and stable in commercial trials and seed production for two years.

Objective Description of the Variety IS 44038

Plant Type

ISI 44038 is plant type Cutting/Leaf

Seed

The seeds are black in color. The seeds do not require light. The seeds are susceptible to heat dormancy.

Cotyledon to Fourth Leaf Stage

The cotyledons are broad in shape. The shape of the fourth leaf is elongated. The length/width index of the fourth leaf is 2/4×10. The apical margin is moderately dentate. The basal margin is moderately dentate. The undulation is medium. The green color is light green. The distribution of the anthocyanin is throughout. The concentration is intense. Rolling is absent. It is uncupped. There is no reflexing.

Mature Leaves

Margin

The incision depth is absent/shallow. The indentation is shallowly dentate. The undulations of the apical margin are strong. The green color is light green.

The anthocyanin distribution is throughout and the concentration is intense. It is large in size. It is glossy. Blistering is absent/slight. The leaf is thin. The trichomes are absent.

Plant

The spread of frame leaves is 18 cm. The head diameter is 16 cm. The head shape is non-heading. The head weight is 240 g. The head firmness is loose. The butt is flat. The midrib is flattened. The diameter at base of head is 13 mm. The ratio of head diameter/core diameter is 10.7. The core height from base of head to apex is 37 mm.

Bolting

The number of days from first water date to seed stalk emergence was 40. The bolting class is medium. The height of mature seed stalk is 70. The spread of bolter plant is 30 cm. The bolter leaves are straight. The margin is entire. The color is light green. The bolter habit of the terminal inflorescence is present. The bolter habit of the lateral shoots is present. The bolter habit of the basal side shoots is absent.

Maturity

The season picked was summer. The earliness of harvest-mature head formation was 25 days.

Adaptation

The primary regions of adaptation are Southwest, North Central, West Coast, Southeast, and Northeast The ISI 44038 adapted in the Southwest in the spring, summer, and fall seasons. It did not adapt in the winter. The soil type was both organic and mineral.

Viral Diseases

The ISI 44038 is susceptible to lettuce mosaic, cucumber mosaic, tomato bushy stunt, turnip mosaic, and lettuce infectious yellows. It is moderately susceptible/moderately resistant to beet western yellows and big vein.

Fungal/Bacterial Diseases

The ISI 44038 is susceptible to corky root rot, botrylis, bacterial leaf spot, powdery mildew, and anthracnose. It is moderately susceptible/moderately resistant to sclerotinla drop, verticillium wilt, and bacterial soft rot. It is resistant to the CAI-CAVI races of downy mildew.

Insects

The ISI 44038 is susceptible to cabbage loopers, root aphids, green peach aphid, and lettuce aphid, and pea leafminer.

Physiological Stresses

The ISI 44038 is susceptible to brown rib. It is moderately susceptible/moderately resistant to tipburn, heat, drought, cold, and salt.

Post Harvest Stress

The ISI 44038 is susceptible to russet spotting, rusty brown discoloration, internal rib necrosis, and brown stain, and pink rib.

Comparisons to ISI 44038

Apache

The most similar variety used as a comparison to ISI 44038 is Apache.

Plant Type

Apache is plant type Cutting/Leaf

Seed

The seeds are black in color. The seeds do not require light. The seeds are susceptible to heat dormancy.

Cotyledon to Fourth Leaf Stage

The cotyledons are broad in shape. The shape of the fourth leaf is elongated. The length/width index of the fourth leaf is 1/9×10. The apical margin is moderately dentate. The basal margin is moderately dentate. The undulation is medium. The green color is medium green. The distribution of the anthocyanin is throughout. The concentration is intense. Rolling is absent. It is uncupped. There is no reflexing.

Mature Leaves

Margin

The incision depth is absent/shallow. The indentation is shallowly dentate. The undulations of the apical margin are strong. The green color is medium green.

The anthocyanin distribution is throughout and the concentration is intense. It is medium in size. It is glossy. Blistering is moderate. The leaf is thin. The trichomes are present.

Plant

The spread of frame leaves is 19 cm. The head diameter is 16 cm. The head shape is non-heading. The head weight is 240 g. The head firmness is loose. The butt is slightly concave. The midrib is flattened. The diameter at base of head is 16 mm. The ratio of head diameter/core diameter is 11.4. The core height from base of head to apex is 60 mm.

Bolting

The number of days from first water date to seed stalk emergence was 43. The bolting class is medium. The height of mature seed stalk is 65. The spread of bolter plant is 27 cm. The bolter leaves are straight. The margin is entire. The color is medium green. The bolter habit of the terminal inflorescence is present. The bolter habit of the lateral shoots is present. The bolter habit of the basal side shoots is absent.

Maturity

The season picked was summer. The earliness of harvest-mature head formation was 29 days.

Viral Diseases

The Apache is susceptible to lettuce mosaic, cucumber mosaic, tomato bushy stunt, turnip mosaic, lettuce infectious yellows, beet western yellows, and big vein.

Fungal/Bacterial Diseases

The Apache is susceptible to corky root rot, botrylis, bacterial leaf spot, powdery mildew, anthracnose, bacterial soft rot and sclerotinla drop. It is moderately susceptible/moderately resistant to verticillium wilt and to the CAI-CAVI races of downy mildew.

Insects

The Apache is susceptible to cabbage loopers, root aphids, green peach aphid, and lettuce aphid, and pea leafminer.

Physiological Stresses

The Apache is susceptible to brown rib. It is moderately susceptible/moderately resistant to tipburn, heat, drought, cold, and salt.

Post Harvest Stress

The Apache is susceptible to russet spotting, rusty brown discoloration, internal rib necrosis, and brown stain, and pink rib.

Lirac

The standard regional check variety used is Lirac.

Plant Type

Lirac is plant type Cutting/Leaf.

Seed

The seeds are black in color. The seeds do not require light. The seeds are susceptible to heat dormancy.

Cotyledon to Fourth Leaf Stage

The cotyledons are broad in shape. The shape of the fourth leaf is elongated. The length/width index of the fourth leaf is 2×10. The apical margin is moderately dentate. The basal margin is moderately dentate. The undulation is medium. The green color is medium green. The distribution of the anthocyanin is throughout. The concentration is moderate. Rolling is absent. It is uncupped. There is no reflexing.

Mature Leaves

Margin

The incision depth is absent/shallow. The indentation is shallowly dentate. The undulations of the apical margin are moderate. The green color is medium green.

The anthocyanin distribution is throughout and the concentration is moderate. It is medium in size. It is glossy. Blistering is moderate. The leaf is thin. The trichomes are absent.

Plant

The spread of frame leaves is 22 cm. The head diameter is 20 cm. The head shape is non-heading. The head weight is 240 g. The head firmness is loose. The butt is flat. The midrib is flattened. The diameter at base of head is 16 mm. The ratio of head diameter/core diameter is 16.2. The core height from base of head to apex is 33 mm.

Bolting

The number of days from first water date to seed stalk emergence was 47. The bolting class is medium. The height of mature seed stalk is 65. The spread of bolter plant is 27 cm. The bolter leaves are straight. The margin is entire. The color is light green. The bolter habit of the terminal inflorescence is present. The bolter habit of the lateral shoots is present. The bolter habit of the basal side shoots is absent.

Maturity

The season picked was summer. The earliness of harvest-mature head formation was 30 days.

Viral Diseases

The Lirac is susceptible to lettuce mosaic, cucumber mosaic, tomato bushy stunt, turnip mosaic, lettuce infectious yellows, beet western yellows, and big vein.

Fungal/Bacterial Diseases

The Lirac is susceptible to corky root rot, botrylis, bacterial leaf spot, powdery mildew, anthracnose, sclerotinla drop, verticillium wilt, and bacterial soft rot. It is resistant to the CAI-CAVI races of downy mildew.

Insects

The Lirac is susceptible to cabbage loopers, root aphids, green peach aphid, and lettuce aphid, and pea leafminer.

Physiological Stresses

The Lirac is susceptible to heat, salt, and brown rib. It is moderately susceptible/moderately resistant to tipburn, drought, and cold.

Post Harvest Stress

The Lirac is susceptible to russet spotting, rusty brown discoloration, internal rib necrosis, and brown stain, and pink rib.

ISI 44272

44272 is a red leaf lettuce variety developed from a hand pollinated cross of the varieties ISI 44009 and ISI 44011, both available from ISI Sementi in Italy. The initial cross was made in Fidenza (PR), Italy. The F1 seed harvested was designated as 33-0501092. The cross was made to produce a variety with dark red color, upright standing and bubbled leaves.

The following year, approximately 40 plants of the F1 seed were planted in Cesena (FC), Italy for seed increase. The block was rogued eliminating the self pollination plants. The F2 seed was harvested individually.

More than 25 F2 populations were planted in a research and development field trial in Cesena (FC), Italy the following year. Individual F2 plants were selected at market maturity for particular distinguishing characteristics in type, size, dark red color, days to bolting, upright standing, bubbled leaf.

The F3 seed were trialed throughout the growing season in years 3 and 4 in Fidenza (PR), Italy.

A selected line was increased in year 5. Early bolting, less dark and smooth plants were removed. The plants were harvested individually and the F5 population showed good stability and uniformity.

The F6 seed was uniform and without variants and showed good bolting resistance. ISI 44272 was evaluated and determined to be uniform and stable in commercial trials and seed production for two years.

Objective Description of the Variety ISI 44272

Plant Type

ISI 44272 is plant type Cutting/Leaf.

Seed

The seeds are black in color. The seeds do not require light. The seeds are susceptible to heat dormancy.

Cotyledon to Fourth Leaf Stage

The cotyledons are broad in shape. The shape of the fourth leaf is elongated. The length/width index of the fourth leaf is 2/2×10. The apical margin is moderately dentate. The basal margin is moderately dentate. The undulation is medium. The green color is medium green. The distribution of the anthocyanin is throughout. The concentration is intense. Rolling is absent. It is uncupped. There is no reflexing.

Mature Leaves

Margin

The incision depth is absent/shallow. The indentation is shallowly dentate. The undulations of the apical margin is strong. The green color is medium green.

The anthocyanin distribution is throughout and the concentration is intense. It is large in size. It is glossy. Blistering is strong. The leaf is thin. The trichomes are absent.

Plant

The spread of frame leaves is 21 cm. The head diameter is 18 cm. The head shape is non-heading. The head weight is 240 g. The head firmness is loose. The butt is flat. The midrib is flattened. The diameter at base of head is 15 mm. The ratio of head diameter/core diameter is 12.0. The core height from base of head to apex is 35 mm.

Bolting

The number of days from first water date to seed stalk emergence was 44. The bolting class is medium. The height of mature seed stalk is 68. The spread of bolter plant is 32 cm. The bolter leaves are straight. The margin is entire. The color is medium green. The bolter habit of the terminal inflorescence is present. The bolter habit of the lateral shoots is present. The bolter habit of the basal side shoots is absent.

Maturity

The season picked was summer. The earliness of harvest-mature head formation was 31 days.

Adaptation

The primary regions of adaptation are Southwest, North Central, West Coast, Southeast, and Northeast. The ISI 44272 adapted in the Southwest in the spring, summer, and fall seasons. It did not adapt in the winter. The soil type was both organic and mineral.

Viral Diseases

The ISI 44272 is susceptible to lettuce mosaic, cucumber mosaic, tomato bushy stunt, turnip mosaic, and lettuce infectious yellows. It is moderately susceptible/moderately resistant to beet western yellows and big vein.

Fungal/Bacterial Diseases

The ISI 44272 is susceptible to corky root rot, botrylis, bacterial leaf spot, powdery mildew, and anthracnose. It is moderately susceptible/moderately resistant to sclerotinla drop, verticillium wilt, and bacterial soft rot. It is resistant to the CAI-CAVI races of downy mildew.

Insects

The ISI 44272 is susceptible to cabbage loopers, root aphids, green peach aphid, and lettuce aphid, and pea leafminer.

Physiological Stresses

The ISI 44272 is susceptible to brown rib. It is moderately susceptible/moderately resistant to tipburn, heat, drought, cold, and salt.

Post Harvest Stress

The ISI 44272 is susceptible to russet spotting, rusty brown discoloration, internal rib necrosis, and brown stain, and pink rib.

Comparisons to ISI 44272

Apache

The most similar variety used as a comparison to ISI 44038 is Apache. Please see description above.

Lirac

The standard regional check variety used is Lirac. Please see description above.

ISI 44301

44301 is a cos lettuce variety developed from a hand pollinated cross of the varieties ISI 44121 and ISI 44099, both available from ISI Sementi in Italy. The initial cross was made in Fidenza (PR), Italy. The F1 seed harvested was designated as 33-0501211. The cross was made to produce a variety with dark green color, upright standing, cold resistance and compact size.

The following year, approximately 30 plants of the F1 seed were planted in Cesena (FC), Italy for seed increase. The block was rogued eliminating the self pollination plants. The F2 seed was harvested individually.

More than 20 F2 populations were planted in a research and development field trial in Cesena (FC), Italy the following year. Individual F2 plants were selected at market maturity for particular distinguishing characteristics in type, size, dark green color, days to bolting, upright standing, cold resistance and compact size.

The F3 seed were trialed throughout the growing season in years 3 and 4 in Fidenza (PR), Italy.

A selected line was increased in year 5. Early bolting, less dark and bigger plants were removed. The plants were harvested individually and the F5 population showed good stability and uniformity.

The F6 seed was uniform and without variants and showed good bolting resistance ISI 44301 was evaluated and determined to be uniform and stable in commercial trials and seed production for two years.

Objective Description of the Variety ISI 44301

Plant Type

ISI 44301 is plant type Cos or Romaine.

Seed

The seeds are white in color. The seeds do not require light. The seeds are susceptible to heat dormancy.

Cotyledon to Fourth Leaf Stage

The cotyledons are broad in shape. The shape of the fourth leaf is elongated. The length/width index of the fourth leaf is 2/5×10. The apical margin is entire. The basal margin is crenate/gnawed. The undulation is medium. The green color is medium green. The distribution of the anthocyanin is absent.

Mature Leaves

Margin

The incision depth is absent/shallow. The indentation is entire. The undulations of the apical margin are absent/slight. The green color is medium green.

The anthocyanin distribution is absent and the concentration is light. It is medium in size. It is dull. Blistering is absent/slight. The leaf thickness is intermediate. The trichomes are absent.

Plant

The spread of frame leaves is 33 cm. The head diameter is 16 cm. The head shape is elongate. The head size class is small. The head per carton is 4. The head weight is 410 g. The head firmness is moderate. The butt is slightly concave. The midrib is moderately raised. The diameter at base of head is 75 mm. The ratio of head diameter/core diameter is 21.3. The core height from base of head to apex is 65 mm.

Bolting

The number of days from first water date to seed stalk emergence was 42. The bolting class is rapid. The height of mature seed stalk is 60. The spread of bolter plant is 32 cm. The bolter leaves are straight. The margin is entire. The color is light green. The bolter habit of the terminal inflorescence is present. The bolter habit of the lateral shoots is present. The bolter habit of the basal side shoots is absent.

Maturity

The season picked was summer. The earliness of harvest-mature head formation was 37 days.

Adaptation

The primary regions of adaptation are Southwest North Central, West Coast, Southeast, and Northeast. The ISI 44301 adapted in the Southwest in the spring, summer, and fall seasons. It did not adapt in the winter. The soil type was both organic and mineral.

Viral Diseases

ISI 44301 is susceptible to lettuce mosaic, cucumber mosaic, tomato bushy stunt, turnip mosaic, and lettuce infectious yellows. It is moderately susceptible/moderately resistant to beet western yellows and big vein.

Fungal/Bacterial Diseases

ISI 44301 is susceptible to corky root rot, botrylis, bacterial leaf spot, powdery mildew, downy mildew, and anthracnose. It is moderately susceptible/moderately resistant to sclerotinla drop, verticillium wilt, and bacterial soft rot.

Insects

ISI 44301 is susceptible to cabbage loopers, root aphids, green peach aphid, and lettuce aphid, and pea leafminer.

Physiological Stresses

ISI 44301 is susceptible to heat, draught, and brown rib. It is moderately susceptible/moderately resistant to tipburn, cold, and salt.

Post Harvest Stress

ISI 44301 is susceptible to russet spotting, rusty brown discoloration, internal rib necrosis, and brown stain, and pink rib.

Comparisons to ISI 44301

Remus

The most similar variety used as a comparison to ISI 44038 is Remus.

Plant Type

ISI 44301 is plant type Cos or Romaine.

Seed

The seeds are white in color. The seeds do not require light. The seeds are susceptible to heat dormancy.

Cotyledon to Fourth Leaf Stage

The cotyledons are broad in shape. The shape of the fourth leaf is elongated. The length/width index of the fourth leaf is 2/6×10. The apical margin is entire. The basal margin is crenate/gnawed. The undulation is slight. The green color is dark green. The distribution of the anthocyanin is absent.

Mature Leaves

Margin

The incision depth is absent/shallow. The indentation is entire. The undulations of the apical margin are absent/slight. The green color is dark green.

The anthocyanin distribution is absent and the concentration is light. It is medium in size. It is moderately glossy. Blistering is absent/slight. The leaf thickness is thick. The trichomes are present.

Plant

The spread of frame leaves is 35 cm. The head diameter is 19 cm. The head shape is elongate. The head size class is medium. The head per carton is 3. The head weight is 400 g. The head firmness is moderate. The butt is slightly concave. The midrib is moderately raised. The diameter at base of head is 80 mm. The ratio of head diameter/core diameter is 23.7. The core height from base of head to apex is 75 mm.

Bolting

The number of days from first water date to seed stalk emergence was 44. The bolting class is medium. The height of mature seed stalk is 65. The spread of bolter plant is 33 cm. The bolter leaves are straight. The margin is entire. The color is dark green. The bolter habit of the terminal inflorescence is present. The bolter habit of the lateral shoots is present. The bolter habit of the basal side shoots is absent.

Maturity

The season picked was summer. The earliness of harvest-mature head formation was 40 days.

Viral Diseases

ISI 44301 is susceptible to lettuce mosaic, cucumber mosaic, tomato bushy stunt turnip mosaic, lettuce infectious yellows, beet western yellows, and big vein.

Fungal/Bacterial Diseases

ISI 44301 is susceptible to corky root rot, botrylis, bacterial leaf spot, powdery mildew, downy mildew, anthracnose, sclerotinla drop, verticillium wilt, and bacterial soft rot.

Insects

ISI 44301 is susceptible to cabbage loopers, root aphids, green peach aphid, and lettuce aphid, and pea leafminer.

Physiological Stresses

ISI 44301 is susceptible to heat, draught, tipburn, salt, and brown rib. It is moderately susceptible/moderately resistant to cold.

Post Harvest Stress

ISI 44301 is susceptible to russet spotting, rusty brown discoloration, internal rib necrosis, and brown stain, and pink rib.

Bacio

The standard regional check variety used is Bacio.

Plant Type

Bacio is plant type Cos or Romaine.

Seed

The seeds are white in color. The seeds do not require light. The seeds are not susceptible to heat dormancy.

Cotyledon to Fourth Leaf Stage

The cotyledons are broad in shape. The shape of the fourth leaf is elongated. The length/width index of the fourth leaf is 2/7×10. The apical margin is entire. The basal margin is crenate/gnawed. The undulation is slight. The green color is dark green. The distribution of the anthocyanin is absent.

Mature Leaves

Margin

The incision depth is absent/shallow. The indentation is entire. The undulations of the apical margin are absent/slight. The green color is dark green.

The anthocyanin distribution is absent. The concentration is light. It is medium in size. It is moderately glossy. Blistering is moderate. The leaf thickness is intermediate. The trichomes are absent.

Plant

The spread of frame leaves is 34 cm. The head diameter is 17 cm. The head shape is elongate. The head size class is medium. The head per carton is 3. The head weight is 430 g. The head firmness is moderate. The butt is slightly concave. The midrib is moderately raised. The diameter at base of head is 85 mm. The ratio of head diameter/core diameter is 20.0. The core height from base of head to apex is 65 mm.

Bolting

The number of days from first water date to seed stalk emergence was 48. The bolting class is slow. The height of mature seed stalk is 63. The spread of bolter plant is 30 cm. The bolter leaves are straight. The margin is entire. The color is dark green. The bolter habit of the terminal inflorescence is present. The bolter habit of the lateral shoots is present. The bolter habit of the basal side shoots is absent.

Maturity

The season picked was summer. The earliness of harvest-mature head formation was 43 days.

Viral Diseases

The Bacio is susceptible to cucumber mosaic, tomato bushy stunt, turnip mosaic, lettuce infectious yellows, beet western yellows, and big vein. It is moderately susceptible/moderately resistant to lettuce mosaic.

Fungal/Bacterial Diseases

The Bacio is susceptible to corky root rot botrylis, bacterial leaf spot powdery mildew, anthracnose, verticillium wilt, and bacterial soft rot. It is moderately susceptible/moderately resistant to sclerotinla drop. It is resistant to downy mildew.

Insects

The Bacio is susceptible to cabbage loopers, root aphids, green peach aphid, and lettuce aphid, and pea leafminer.

Physiological Stresses

The Bacio is susceptible to salt, cold, and brown rib. It is moderately susceptible/moderately resistant to tipburn, heat, and drought.

Post Harvest Stress

The Bacio is susceptible to russet spotting, rusty brown discoloration, internal rib necrosis, and brown stain, and pink rib.

ISI 44232

ISI 44232 is a cos lettuce variety developed from a hand pollinated cross of the varieties ISI 44121 and ISI 44099, both available from ISI Sementi in Italy. The initial cross was made in Fidenza (PR), Italy. The F1 seed harvested was designated as 33-0501211. The cross was made to produce a variety with dark green color, cold resistance and compact and heavy head.

The following year, approximately 30 plants of the F1 seed were planted in Cesena (FC), Italy for seed increase. The block was rogued eliminating the self pollination plants. The F2 seed was harvested individually.

More than 20 F2 populations were planted in a research and development field trial in Cesena (FC), Italy the following year. Individual F2 plants were selected at market maturity for particular distinguishing characteristics in type, size, dark green color, days to bolting, cold resistance and heavy head.

The F3 seed were trialed throughout the growing season in years 3 and 4 in Fidenza (PR), Italy.

A selected line was increased in year 5. Early bolting, less dark and smaller plants were removed. The plants were harvested individually and the F5 population showed good stability and uniformity.

The F6 seed was uniform and without variants and showed good bolting resistance. ISI 44232 was evaluated and determined to be uniform and stable in commercial trials and seed production for two years.

Objective Description of the Variety ISI 44232

ISI 44232 is plant type Cos or Romaine.

Seed

The seeds are white in color. The seeds do not require light. The seeds are susceptible to heat dormancy.

Cotyledon to Fourth Leaf Stage

The cotyledons are broad in shape. The shape of the fourth leaf is elongated. The length/width index of the fourth leaf is 3×10. The apical margin is entire. The basal margin is crenate/gnawed. The undulation is medium. The green color is medium green. The distribution of the anthocyanin is absent.

Mature Leaves

Margin

The incision depth is absent/shallow. The indentation is entire. The undulations of the apical margin are absent/slight. The green color is medium green.

The anthocyanin distribution is absent and the concentration is light. It is medium in size. It is moderately glossy. Blistering is moderate. The leaf thickness is intermediate. The trichomes are absent.

Plant

The spread of frame leaves is 37 cm. The head diameter is 18 cm. The head shape is elongate. The head size class is medium. The head per carton is 3. The head weight is 450 g. The head firmness is moderate. The butt is slightly concave. The midrib is moderately raised. The diameter at base of head is 90 mm. The ratio of head diameter/core diameter is 20.0. The core height from base of head to apex is 70 mm.

Bolting

The number of days from first water date to seed stalk emergence was 46. The bolting class is medium. The height of mature seed stalk is 68. The spread of bolter plant is 35 cm. The bolter leaves are straight. The margin is entire. The color is medium green. The bolter habit of the terminal inflorescence is present. The bolter habit of the lateral shoots is present. The bolter habit of the basal side shoots is absent.

Maturity

The season picked was summer. The earliness of harvest-mature head formation was 38 days.

Adaptation

The primary regions of adaptation are Southwest, North Central, West Coast, Southeast and Northeast. The ISI 44232 adapted in the Southwest in the spring and summer seasons. It did not adapt in the fall and winter. The soil type was both organic and mineral.

Viral Diseases

The ISI 44232 is susceptible to lettuce mosaic, cucumber mosaic, tomato bushy stunt, turnip mosaic, beet western yellows, and lettuce infectious yellows. It is moderately susceptible/moderately resistant to big vein.

Fungal/Bacterial Diseases

The ISI 44232 is susceptible to corky root rot, botrylis, bacterial leaf spot, powdery mildew, and anthracnose. It is moderately susceptible/moderately resistant to sclerotinla drop, verticillium wilt and bacterial soft rot. It is resistant to the CAI-CAVI races of downy mildew.

Insects

The ISI 44232 is susceptible to cabbage loopers, root aphids, green peach aphid, and lettuce aphid, and pea leafminer.

Physiological Stresses

The ISI 44232 is susceptible to salt and brown rib. It is moderately susceptible/moderately resistant to tipburn, heat, drought, and cold.

Post Harvest Stress

The ISI 44232 is susceptible to russet spotting, rusty brown discoloration, internal rib necrosis, and brown stain, and pink rib.

Comparisons to ISI 44232

Remus

The most similar variety used as a comparison to ISI 44232 is Remus. Please see description above.

Bacio

The standard regional check variety used is Bacio. Please see description above.

ISI 44251

44251 is a cos lettuce variety developed from a hand pollinated cross of the varieties ISI 44001 and ISI 44099, both available from ISI Sementi in Italy. The initial cross was made in Fidenza (PR), Italy. The F1 seed harvested was designated as 33-0501237. The cross was made to produce a variety with dark green color, cold resistance, and big size.

The following year, approximately 40 plants of the F1 seed were planted in Cesena (FC), Italy for seed increase. The block was rogued eliminating the self pollination plants. The F2 seed was harvested individually.

More than 30 F2 populations were planted in a research and development field trial in Cesena (FC), Italy the following year. Individual F2 plants were selected at market maturity for particular distinguishing characteristics in type, size, dark green color, cold resistance and big size.

The F3 seed were trialed throughout the growing season in years 3 and 4 in Fidenza (PR), Italy.

A selected line was increased in year 5. Early bolting, less dark and smaller plants were removed. The plants were harvested individually and the F5 population showed good stability and uniformity.

The F6 seed was uniform and without variants and showed good bolting resistance ISI 44251 was evaluated and determined to be uniform and stable in commercial trials and seed production for two years.

Objective Description of the Variety ISI 44251

ISI 44251 is plant type Cos or Romaine.

Seed

The seeds are white in color. The seeds do not require light. The seeds are susceptible to heat dormancy.

Cotyledon to Fourth Leaf Stage

The cotyledons are broad in shape. The shape of the fourth leaf is elongated. The length/width index of the fourth leaf is 3/3×10. The apical margin is entire. The basal margin is crenate/gnawed. The undulation is medium. The green color is dark green. The distribution of the anthocyanin is absent.

Mature Leaves

Margin

The incision depth is absent/shallow. The indentation is entire. The undulations of the apical margin are absent/slight. The green color is dark green.

The anthocyanin distribution is absent and the concentration is light. It is large in size. It is moderately glossy. Blistering is moderate. The leaf thickness is thick. The trichomes are absent.

Plant

The spread of frame leaves is 40 cm. The head diameter is 23 cm. The head shape is elongate. The head size class is medium. The head per carton is 3. The head weight is 470 g. The head firmness is moderate. The butt is slightly concave. The midrib is moderately raised. The diameter at base of head is 90 mm. The ratio of head diameter/core diameter is 25.5. The core height from base of head to apex is 70 mm.

Bolting

The number of days from first water date to seed stalk emergence was 41. The bolting class is medium. The height of mature seed stalk is 71. The spread of bolter plant is 35 cm. The bolter leaves are straight. The margin is entire. The color is dark green. The bolter habit of the terminal inflorescence is present. The bolter habit of the lateral shoots is present. The bolter habit of the basal side shoots is absent.

Maturity

The season picked was summer. The earliness of harvest-mature head formation was 37 days.

Adaptation

The primary regions of adaptation are Southwest, North Central, West Coast, Southeast, and Northeast. The ISI 44251 adapted in the Southwest in the spring, fall, and summer seasons. It did not adapt in the winter. The soil type was both organic and mineral.

Viral Diseases

ISI 44251 is susceptible to lettuce mosaic, cucumber mosaic, tomato bushy stunt, turnip mosaic, and lettuce infectious yellows. It is moderately susceptible/moderately resistant to big vein and beet western yellow.

Fungal/Bacterial Diseases

ISI 44251 is susceptible to corky root rot, botrylis, bacterial leaf spot, powdery mildew, and anthracnose. It is moderately susceptible/moderately resistant to sclerotinla drop, verticillium wilt, and bacterial soft rot. It is resistant to the CAI-CAVI races of downy mildew.

Insects

The ISI 44251 is susceptible to cabbage loopers, root aphids, green peach aphid, and lettuce aphid, and pea leafminer.

Physiological Stresses

The ISI 44251 is susceptible to heat, draught, and brown rib. It is moderately susceptible/moderately resistant to tipburn, salt, and cold.

Post Harvest Stress

ISI 44251 is susceptible to russet spotting, rusty brown discoloration, internal rib necrosis, and brown stain, and pink rib.

Comparisons to ISI 44251

Remus

The most similar variety used as a comparison to ISI 44251 is Remus. Please see description above.

Bacio

The standard regional check variety used is Bacio. Please see description above.

ISI 44236

44236 is a cos lettuce variety developed from a hand pollinated cross of the varieties ISI 44001 and ISI 44099, both available from ISI Sementi in Italy. The initial cross was made in Fidenza (PR), Italy. The F1 seed harvested was designated as 33-0501237. The cross was made to produce a variety with medium green color, bolting resistance, tip burn tolerance and open head.

The following year, approximately 50 plants of the F1 seed were planted in Cesena (FC), Italy for seed increase. The block was rogued eliminating the self pollination plants. The F2 seed was harvested individually.

More than 30 F2 populations were planted in a research and development field trial in Cesena (FC), Italy the following year. Individual F2 plants were selected at market maturity for particular distinguishing characteristics in type, size, medium green color, bolting resistance and open head.

The F3 seed were trialed throughout the growing season in years 3 and 4 in Fidenza (PR), Italy.

A selected line was increased in year 5. Early bolting, less dark and plants with closed heads were removed. The plants were harvested individually and the F5 population showed good stability and uniformity.

The F6 seed was uniform and without variants and showed good bolting resistance. ISI 44236 was evaluated and determined to be uniform and stable in commercial trials and seed production for two years.

Objective Description of the Variety ISI 44236

ISI 44236 is plant type Cos or Romaine.

Seed

The seeds are white in color. The seeds do not require light. The seeds are susceptible to heat dormancy.

Cotyledon to Fourth Leaf Stage

The cotyledons are broad in shape. The shape of the fourth leaf is elongated. The length/width index of the fourth leaf is 2/3×10. The apical margin is entire. The basal margin is crenate/gnawed. The undulation is medium. The green color is medium green. The distribution of the anthocyanin is absent and the concentration is light. Rolling is absent. It is uncupped. There is no reflexing.

Mature Leaves

Margin

The incision depth is absent/shallow. The indentation is entire. The undulations of the apical margin are absent/slight. The green color is light green.

The anthocyanin distribution is absent and the concentration is light. It is medium in size. It is moderately glossy. Blistering is moderate. The leaf thickness is intermediate. The trichomes are absent.

Plant

The spread of frame leaves is 42 cm. The head diameter is 21 cm. The head shape is elongate. The head size class is medium. The head per carton is 3. The head weight is 440 g. The head firmness is moderate. The butt is slightly concave. The midrib is moderately raised. The diameter at base of head is 80 mm. The ratio of head diameter/core diameter is 26.2. The core height from base of head to apex is 65 mm.

Bolting

The number of days from first water date to seed stalk emergence was 50. The bolting class is slow. The height of mature seed stalk is 60. The spread of bolter plant is 32 cm. The bolter leaves are straight. The margin is entire. The color is light green. The bolter habit of the terminal inflorescence is present. The bolter habit of the lateral shoots is present. The bolter habit of the basal side shoots is absent.

Maturity

The season picked was sunmer. The earliness of harvest-mature head formation was 44 days.

Adaptation

The primary regions of adaptation are Southwest, North Central, West Coast, Southeast, and Northeast. The ISI 44236 adapted in the Southwest in the spring, fall, and summer seasons. It did not adapt in the winter. The soil type was both organic and mineral.

Viral Diseases

The ISI 44236 is susceptible to beet western yellows, cucumber mosaic, tomato bushy stunt, turnip mosaic, and lettuce infectious yellows. It is moderately susceptible/moderately resistant to big vein. It is resistant to lettuce mosaic.

Fungal/Bacterial Diseases

The ISI 44236 is susceptible to corky root rot, botrylis, bacterial leaf spot powdery mildew, and anthracnose. It is moderately susceptible/moderately resistant to sclerotinla drop, verticillium wilt and bacterial soft rot. It is resistant to the CAI-CAVI races of downy mildew.

Insects

The ISI 44236 is susceptible to cabbage loopers, root aphids, green peach aphid, and lettuce aphid, and pea leafminer.

Physiological Stresses

The ISI 44236 is susceptible to cold and brown rib. It is moderately susceptible/moderately resistant to tipburn, heat, drought, and salt.

Post Harvest Stress

The ISI 44236 is susceptible to russet spotting, rusty brown discoloration, internal rib necrosis, and brown stain, and pink rib.

Comparisons to ISI 44236

Remus

The most similar variety used as a comparison to ISI 44236 is Remus. Please see description above.

Bacio

The standard regional check variety used is Bacio. Please see description above.

ISI 44159

44159 is a medium cos lettuce variety developed from a hand pollinated cross of the varieties ISI 44201 and Little Gem, both available from ISI Sementi in Italy. The initial cross was made in Fidenza (PR), Italy. The F1 seed harvested was designated as 33-0501312. The cross was made to produce a variety with medium green color, bolting resistance, tip burn tolerance and intermediate size between little gem and normal cos.

The following year, approximately 45 plants of the F1 seed were planted in Cesena (FC), Italy for seed increase. The block was rogued eliminating the self pollination plants. The F2 seed was harvested individually.

More than 35 F2 populations were planted in a research and development field trial in Cesena (FC), Italy the following year. Individual F2 plants were selected at market maturity for particular distinguishing characteristics in type, intermediate size, medium green color, bolting resistance and tip burn tolerance.

The F3 seed were trialed throughout the growing season in years 3 and 4 in Fidenza (PR), Italy.

A selected line was increased in year 5. Early bolting, less dark, and plants that were either too large or too small were removed. The plants were harvested individually and the F5 population showed good stability and uniformity.

The F6 seed was uniform and without variants and showed good bolting resistance. ISI 44159 was evaluated and determined to be uniform and stable in commercial trials and seed production for two years.

Objective Description of the Variety ISI 44159

ISI 44159 is plant type Cos or Romaine.

Seed

The seeds are white in color. The seeds do not require light. The seeds are susceptible to heat dormancy.

Cotyledon to Fourth Leaf Stage

The cotyledons are broad in shape. The shape of the fourth leaf is elongated. The length/width index of the fourth leaf is 2/8×10. The apical margin is entire. The basal margin is crenate/gnawed. The undulation is medium. The green color is medium green. The distribution of the anthocyanin is absent.

Mature Leaves

Margin

The incision depth is absent/shallow. The indentation is entire. The undulations of the apical margin are absent/slight. The green color is medium green.

The anthocyanin distribution is absent and the concentration is light. It is medium in size. It is glossy. Blistering is moderate. The leaf thickness is intermediate. The trichomes are absent.

Plant

The spread of frame leaves is 33 cm. The head diameter is 16 cm. The head shape is elongate. The head size class is medium. The head per carton is 4. The head weight is 470 g. The head firmness is firm. The butt is slightly concave. The midrib is moderately raised. The diameter at base of head is 75 mm. The ratio of head diameter/core diameter is 21.3. The core height from base of head to apex is 63 mm.

Bolting

The number of days from first water date to seed stalk emergence was 45. The bolting class is medium. The height of mature seed stalk is 60. The spread of bolter plant is 30 cm. The bolter leaves are straight. The margin is entire. The color is dark green. The bolter habit of the terminal inflorescence is present. The bolter habit of the lateral shoots is present. The bolter habit of the basal side shoots is absent.

Maturity

The season picked was summer. The earliness of harvest-mature head formation was 41 days.

Adaptation

The primary regions of adaptation are Southwest, North Central, West Coast, Southeast, and Northeast. The ISI 44159 adapted in the Southwest in the spring and summer seasons. It did not adapt in the fall and winter. The soil type was both organic and mineral.

Viral Diseases

ISI 44159 is susceptible to cucumber mosaic, tomato bushy stunt, turnip mosaic, and lettuce infectious yellows. It is moderately susceptible/moderately resistant to beet western yellows and big vein. It is resistant to lettuce mosaic.

Fungal/Bacterial Diseases

ISI 44159 is susceptible to corky root rot, botrylis, powdery mildew, and anthracnose. It is moderately susceptible/moderately resistant to sclerotinla drop, verticillium wilt, bacterial leaf spot, and bacterial soft rot. It is resistant to the CAI-CAVI races of downy mildew.

Insects

ISI 44159 is susceptible to cabbage loopers, root aphids, green peach aphid, and lettuce aphid, and pea leafminer.

Physiological Stresses

ISI 44159 is susceptible to drought, salt, and brown rib. It is moderately susceptible/moderately resistant to tipburn, heat, and cold.

Post Harvest Stress

ISI 44159 is susceptible to russet spotting, rusty brown discoloration, internal rib necrosis, and brown stain, and pink rib.

Comparisons to ISI 44159

Remus

The most similar variety used as a comparison to ISI 44159 is Remus. Please see description above.

Bacio

The standard regional check variety used is Bacio. Please see description above.

ISI 49999

ISI 49999 is a multileaf lettuce variety developed from a hand pollinated cross of the varieties ISI 49113 and ISI 49201, both available from ISI Sementi in Italy. The initial cross was made in Fidenza (PR), Italy. The F1 seed harvested was designated as 33-0501401. The cross was made to produce a variety with dark green color, tip burn tolerance, deeply incised leaf and big size.

The following year, approximately 40 plants of the F1 seed were planted in Cesena (FC), Italy for seed increase. The block was rogued eliminating the self pollination plants. The F2 seed was harvested individually.

More than 25 F2 populations were planted in a research and development field trial in Cesena (FC), Italy the following year. Individual F2 plants were selected at market maturity for particular distinguishing characteristics in type, big size, dark green color and tip burn tolerance.

The F3 seed were trialed throughout the growing season in years 3 and 4 in Fidenza (PR), Italy.

A selected line was increased in year 5. Early bolting, less dark and plants with entire leaf were removed. The plants were harvested individually and the F5 population showed good stability and uniformity.

The F6 seed was uniform and without variants and showed good bolting resistance. ISI 49999 was evaluated and determined to be uniform and stable in commercial trials and seed production for two years.

Objective Description of the Variety ISI 49999

Plant Type

ISI 49999 is plant type Cutting/Leaf.

Seed

The seeds are black in color. The seeds do not require light. The seeds are susceptible to heat dormancy.

Cotyledon to Fourth Leaf Stage

The cotyledons are intermediate in shape. The shape of the fourth leaf is pinnately lobed. The length/width index of the fourth leaf is 1/2×10. The apical margin is incised. The basal margin is incised. The undulation is marked. The green color is medium green. The distribution of the anthocyanin is absent.

Mature Leaves

Margin

The incision depth is deep. The indentation is crenate. The undulations of the apical margin are strong. The green color is medium green.

The anthocyanin distribution is absent. The concentration is light. It is medium in size. It is moderately glossy. There is slight/absent blistering. The leaf is thin. The trichomes are absent.

Plant

The spread of frame leaves is 30 cm. The head diameter is 35 cm. The head shape is non-heading. The head weight is 330 g. The head firmness is loose. The butt is slightly concave. The midrib is moderately raised. The diameter at base of head is 60 mm. The ratio of head diameter/core diameter is 58.3. The core height from base of head to apex is 55 mm.

Bolting

The number of days from first water date to seed stalk emergence was 37. The bolting class is rapid. The height of mature seed stalk is 67. The spread of bolter plant is 27 cm. The bolter leaves are curved. The margin is dentate. The color is medium green. The bolter habit of the terminal inflorescence is present. The bolter habit of the lateral shoots is present. The bolter habit of the basal side shoots is absent.

Maturity

The season picked was summer. The earliness of harvest-mature head formation was 31 days.

Adaptation

The primary regions of adaptation are Southwest North Central, West Coast, Southeast, and Northeast. The ISI 49999 adapted in the Southwest in the spring, summer, and fall seasons. It did not adapt in the winter. The soil type was both organic and mineral.

Viral Diseases

ISI 49999 is susceptible to lettuce mosaic, cucumber mosaic, tomato bushy stunt, turnip mosaic, and lettuce infectious yellows. It is moderately susceptible/moderately resistant to big vein and beet western yellows.

Fungal/Bacterial Diseases

ISI 49999 is susceptible to corky root rot, botrytis, bacterial leaf spot, powdery mildew, and anthracnose. It is moderately susceptible/moderately resistant to scierotinla drop, bacterial soft rot, and verticillium wilt. It is resistant to the CAI-CAVI races of downy mildew.

Insects

ISI 49999 is susceptible to cabbage loopers, root aphids, green peach aphid, and lettuce aphid, and pea leafminer.

Physiological Stresses

ISI 49999 is susceptible to heat, drought, and brown rib. It is moderately susceptible/moderately resistant to tipburn, cold, and salt.

Post Harvest Stress

ISI 49999 is susceptible to russet spotting, rusty brown discoloration, internal rib necrosis, and brown stain. It is moderately susceptible/moderately resistant to pink rib.

Comparisons to ISI 49999

Tango

The most similar variety used as a comparison to ISI 49999 is Tango.

Plant Type

Tango is plant type Cutting/Leaf.

Seed

The seeds are white in color. The seeds do not require light. The seeds are susceptible to heat dormancy.

Cotyledon to Fourth Leaf Stage

The cotyledons are intermediate in shape. The shape of the fourth leaf is pinnately lobed. The length/width index of the fourth leaf is 1×10. The apical margin is incised. The basal margin is incised. The undulation is marked. The green color is yellow green. The distribution of the anthocyanin is absent.

Mature Leaves

Margin

The incision depth is deep. The indentation is crenate. The undulations of the apical margin are strong. The green color is very light green.

The anthocyanin distribution is absent and the concentration is light. It is small in size. It is moderately glossy. There is slight/absent blistering. The leaf is thin. The trichomes are absent.

Plant

The spread of frame leaves is 25 cm. The head diameter is 25 cm. The head shape is non-heading. The head size class is small. The head weight is 270 g. The head firmness is loose. The butt is slightly concave. The midrib is moderately raised. The diameter at base of head is 60 mm. The ratio of head diameter/core diameter is 41.6. The core height from base of head to apex is 55 mm.

Bolting

The number of days from first water date to seed stalk emergence was 35. The bolting class is rapid. The height of mature seed stalk is 65. The spread of bolter plant is 25 cm. The bolter leaves are curved. The margin is dentate. The color is light green. The bolter habit of the terminal inflorescence is present. The bolter habit of the lateral shoots is present. The bolter habit of the basal side shoots is absent.

Maturity

The season picked was summer. The earliness of harvest-mature head formation was 30 days.

Viral Diseases

The Tango is susceptible to lettuce mosaic, cucumber mosaic, tomato bushy stunt, turnip mosaic, and lettuce infectious yellows, big vein, and beet western yellows.

Fungal/Bacterial Diseases

The Tango is susceptible to corky root rot botrytis, bacterial leaf spot, powdery mildew, and anthracnose, sclerotinla drop, bacterial soft rot, and the CAI-CAVI races of downy mildew. It is moderately susceptible/moderately resistant to verticillium wilt.

Insects

The Tango is susceptible to cabbage loopers, root aphids, green peach aphid, and lettuce aphid, and pea leafminer.

Physiological Stresses

The Tango is susceptible to heat, drought and brown rib. It is moderately susceptible/moderately resistant to tipburn, cold, and salt.

Post Harvest Stress

The Tango is susceptible to russet spotting, rusty brown discoloration, internal rib necrosis, and brown stain. It is moderately susceptible/moderately resistant to pink rib.

Guadalupe

The standard regional check variety used is Guadalupe.

Plant Type

Guadalupe is plant type Cutting/Leaf.

Seed

The seeds are black in color. The seeds do not require light. The seeds are susceptible to heat dormancy.

Cotyledon to Fourth Leaf Stage

The cotyledons are intermediate in shape. The shape of the fourth leaf is pinnately lobed. The length/width index of the fourth leaf is 1×10. The apical margin is incised. The basal margin is incised. The undulation is marked. The green color is yellow green. The distribution of the anthocyanin is absent.

Mature Leaves

Margin

The incision depth is deep. The indentation is crenate. The undulations of the apical margin are strong. The green color is very light green.

The anthocyanin distribution is absent and the concentration is light. It is small in size. It is moderately glossy. There is slight/absent blistering. The leaf is thin. The trichomes are absent.

Plant

The spread of frame leaves is 20 cm. The head diameter is 20 cm. The head shape is non-heading. The head size class is small. The head weight is 220 g. The head firmness is loose. The butt is slightly concave. The midrib is moderately raised. The diameter at base of head is 50 mm. The ratio of head diameter/core diameter is 40.0. The core height from base of head to apex is 45 mm.

Bolting

The number of days from first water date to seed stalk emergence was 36. The bolting class is rapid. The height of mature seed stalk is 55. The spread of bolter plant is 22 cm. The bolter leaves are curved. The margin is dentate. The color is light green. The bolter habit of the terminal inflorescence is present. The bolter habit of the lateral shoots is present. The bolter habit of the basal side shoots is absent.

Maturity

The season picked was summer. The earliness of harvest-mature head formation was 28 days.

Viral Diseases

The Guadalupe is susceptible to lettuce mosaic, cucumber mosaic, tomato bushy stunt, turnip mosaic, and lettuce infectious yellows, big vein, and beet western yellows.

Fungal/Bacterial Diseases

The Guadalupe is susceptible to corky root rot, botrytis, bacterial leaf spot, powdery mildew, anthracnose, sclerotinla drop, and bacterial soft rot. It is moderately susceptible/moderately resistant to verticillium wilt. It is resistant to the CAI-CAVI races of downy mildew.

Insects

The Guadalupe is susceptible to cabbage loopers, root aphids, green peach aphid, and lettuce aphid, and pea leafminer.

Physiological Stresses

The Guadalupe is susceptible to heat, drought, and brown rib. It is moderately susceptible/moderately resistant to tipburn, cold, and salt.

Post Harvest Stress

The Guadalupe is susceptible to russet spotting, rusty brown discoloration, internal rib necrosis, and brown stain. It is moderately susceptible/moderately resistant to pink rib.

DEPOSIT INFORMATION

Applicants have made available to the public without restriction a deposit of at least 2500 seeds of lettuce variety ISI 45125 with the American Type Culture Collection (ATCC), P.O. Box 1549, MANASSAS, Va. 20108 USA, with a deposit on Jan. 25, 2007, which has been assigned ATCC number PTA-8182.

The deposit will be maintained in the ATCC depository, which is a public depository, for a period of 30 years, or 5 years after the most recent request, or for the effective life of the patent, whichever is longer, and will be replaced if the deposit becomes nonviable during that period.

The invention claimed is:

1. A lettuce seed designated as ISI 45125 having ATCC Accession Number PTA-8182.
2. A lettuce plant produced by growing the seed of claim 1.
3. A plant part from the plant of claim 2.
4. The plant part of claim 3 wherein said part is a head.
5. The plant part of claim 3 wherein said part is a leaf or a portion thereof.
6. A lettuce plant having all the physiological and morphological characteristics of the lettuce plant of claim 2.
7. A plant part from the plant of claim 6.
8. The plant part of claim 7 wherein said part is a head.
9. The plant part of claim 7 wherein said part is a leaf or a portion thereof.
10. An $F_1$ hybrid lettuce plant having ISI 45125 as a parent where ISI 45125 is grown from the seed of claim 1.
11. Pollen of the plant of claim 2.
12. An ovule of the plant of claim 2.
13. A tissue culture of the plant of claim 2.
14. A method of making lettuce seeds comprised of crossing the plant of claim 2 with another lettuce plant and harvesting seed therefrom.
15. A method of making lettuce variety ISI 45125, said method comprising selecting seeds from the cross of one ISI 45125 plant with another ISI 45125 plant, a sample of ISI 45125 lettuce seed having been deposited under ATCC Accession Number PTA-8182.

* * * * *